United States Patent de Winter et al.

Patent Number: 4,473,564
Date of Patent: Sep. 25, 1984

[54] 19-THIO-ANDROSTANE DERIVATIVES

[75] Inventors: Max S. de Winter; Pieter J. N. van Luit, both of Oss, Netherlands

[73] Assignee: Akzo N.V., Arnhem, Netherlands

[21] Appl. No.: 512,997

[22] Filed: Jul. 12, 1983

[51] Int. Cl.³ .............................................. A61K 31/56
[52] U.S. Cl. .................................... 424/238; 424/243; 260/397.4
[58] Field of Search ...................................... 260/397.4

[56] References Cited

FOREIGN PATENT DOCUMENTS 1132430 10/1968 United Kingdom ............. 260/397.4

Primary Examiner—Elbert L. Roberts
Attorney, Agent, or Firm—Abelman, Fryne, Rezac & Schwab

[57] ABSTRACT

The invention relates to novel 19-thio-androstane derivatives having the general formula:

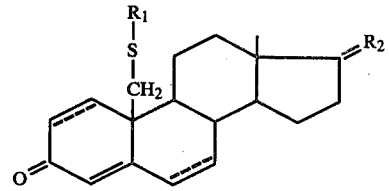

and the 4,5-dihydro analogues thereof, wherein $R_1$ = H, hydrocarbyl(1-4C), aralkyl(7-9C), aryl(6-9C) or acyl derived from an organic carboxylic acid having 1-18 C atoms;

$R_2$ = O, $\alpha R_4(\beta R_3)$ or an acetal group;

$R_3$ = a free, esterified or etherified hydroxyl group; and $R_4$ = H or hydrocarbyl(1-4C);

and wherein the broken lines indicate the optional presence of a double bond in the 1,2-position and/or 6,7-position, and to processes for obtaining same.

The novel compounds possess aromatase-inhibiting properties.

19 Claims, No Drawings

19-THIO-ANDROSTANE DERIVATIVES

The invention relates to novel 19-thio-androstane derivatives, in particular to novel 19-thio-Δ4-androsten-3-one derivatives, which moreover are substituted in the 17-position. The invention also relates to the use of these new compounds as inhibitors of the biosynthesis of oestrogens (aromatase-inhibitors) and to pharmaceutical preparations which contain these androstane derivatives as the active constituent.

The conversion of androgens to oestrogens is a physiological important reaction in the body, especially in that of women. This conversion takes place via a series of reactions, which are collectively referred to by the term: aromatisation. In this aromatisation, a steroidal 3-oxo-Δ4-10-methyl system is converted to an aromatic (phenolic) ring A. In this, enzymes play an important role. The group of enzymes responsible for aromatisation, or one enzyme from this group, is referred to by the name aromatase.

In a normally functioning, healthy body there is an optimum balance between androgens and oestrogens and aromatisation takes place as required in order to maintain this balance as far as possible. Under normal circumstances aromatisation takes place in the body in various tissues: in the ovaries of the woman, in peripheral tissues, such as adipose tissue and muscular tissue, and (albeit to a lesser degree) in the adrenal cortex, the hypothalamus and the brain.

There are clinical indications which are due to an excessive production of oestrogens (hyperoestrogenicity). Thus, for example, women in the peri-menopause have a greater risk of neoplasms (breast cancer or uterine cancer), due to a chronic effect of an excess of oestrogens which occurs in the peri-menopause. During the reproductive years, obesity in women is often accompanied by anovulation, which is probably a consequence of excessive aromatisation in adipose tissue, and hence excessive oestrogen production. In men also an excessive oestrogen production or a too high estrogen/androgen ratio in peripheral or other tissue can give rise to complaints (gynaecomastia in adolescents, prostatic hypertrophy).

For therapeutic and/or prophylactic treatment of hyperoestrogenicity, aromatase-inhibitors have been proposed, thus substances which inhibit the action of aromatase. Compared to the anti-oestrogenically active substances which have also been proposed for this purpose, aromatase-inhibitors have the advantage that the production of oestrogens can be regulated with them, without completely blocking the effect thereof on target organs. Thus, aromatase inhibitors can also advantageously be used for the prophylaxis and/or therapeutic treatment of prostatic hyperplasia caused by a shifting of the oestrogen/androgen ratio to higher values.

Known substances which have an aromatase-inhibiting action are, for example, testolactone (U.S. Pat. No. 2,744,120), 4-hydroxy-Δ4-androstene-3,17-dione and esters thereof (see, for example, U.S. Pat. No. 4,235,893), 10-(1,2-propadienyl)-Δ4-oestrene-3,17-dione (U.S. Pat. No. 4,289,762) and 10-(2-propynyl)-Δ4-oestrene-3,17-dione (J.A.C.S. 1981, 103, 3221 and U.S. Pat. No. 4,322,416).

A new group of androstane derivatives having aromatase-inhibiting properties have now been found, i.e. novel 19-thio-androstane derivatives having the general formula:

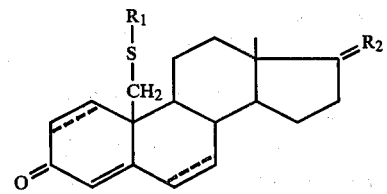

and the 4,5-dihydro analogues thereof, wherein
$R_1$ = H, hydrocarbyl(1-4C), aralkyl(7-9C), aryl(6-9C) or acyl derived from an organic carboxylic acid having 1-18 C atoms;
$R_2$ = O, $\alpha R_4(\beta R_3)$ or an acetal group;
$R_3$ = a free, esterified or etherified hydroxyl group; and
$R_4$ = H or hydrocarbyl(1-4C) and is preferably H;
and wherein the broken lines indicate the optional presence of a double bond in the 1,2-position and/or 6,7-position.

The hydrocarbyl(1-4C) group ($R_1$ or $R_4$) can for example be methyl, ethyl, vinyl, ethinyl, propyl, 2-propenyl, butyl and branched analogues thereof.

The aralkyl group is, for example, benzyl or phenylethyl.

The aryl group is, for example, phenyl, tolyl or xylyl, and is preferably phenyl.

$R_1$ is preferably methyl or ethyl and most preferably methyl.

$R_2$ is preferably O.

$R_3$, if present, is preferably OH.

$R_4$ is preferably H and, when present as hydrocarbyl group, is preferably ethinyl or allyl.

The 4,5-dihydro analogues are preferably the 5α-H compounds.

The acyl group which is optionally present in the 19-substituent or in position 17 can be derived from, for example, acetic acid, propionic acid, butyric acid, trimethylacetic acid, phenylacetic acid, cyclopentylpropionic acid, cyclo-octyl acetic acid, cyclo-octyl carboxylic acid, phenylpropionic acid, valeric acid, caproic acid, pelargonic acid, lauric acid, palmitic acid, benzoic acid or succinic acid.

The acetal group which is optionally present in position 17 can for example be a dialkoxy group, such as dimethoxy, or an alkylenedioxy group, such as ethylenedioxy, propylenedioxy or neopentylenedioxy.

The ether group which is optionally present in position 17 can be an alkyl ether, such as a methyl ether, ethyl ether, cyclopentyl ether, cyclohexenyl ether or the like, an aromatic ether, such as, for example, a benzyl ether, or a heterocyclic ether, such as, for example, a tetrahydropyranyl ether.

The invention also relates to the use of the novel compounds as agents for inhibiting the biosynthesis of oestrogens, i.e. as aromatase inhibitors. The novel compounds can therefore be used in clinical indications where it is desired that the biosynthesis of oestrogen should be inhibited or suppressed, as has already been indicated above.

The invention moreover relates to pharmaceutical preparations having aromatase-inhibiting properties, which contain, as the active constituent, one or more of the novel 19-thio-androstane derivatives. The novel compounds can be administered in the conventional manner, in combination with pharmaceutical auxiliaries, orally, enterally or locally (topically), in the form of tablets, pills, dragees, pastilles, powders, emulsions, suspensions, solutions, suppositories, implants, ointments, creams or lotions. The forms for administration can be prepared in accordance with known galenical procedures.

The novel 19-thio-androstane derivatives can be prepared in a manner known per se.

For example, it is possible to start from a 19-sulphonate (for instance, a 19-tosylate or 19-mesylate) or a 19-halo-derivative (for instance 19-bromo- or 19-iodo-derivative) of a 3-oxo-$\Delta^4$- or 3-hydroxy-$\Delta^5$-androstene and to treat this with a metal salt (preferably a lithium sodium or potassium salt) of an alkanethiol or of a thiocarboxylic acid. In this way, a 19-alkylthio- or 19-acylthio-androstane compound is obtained. If this reaction is carried out with potassium thioacetate, the 19-acetylthio compound is obtained, which in itself is again an interesting starting material for the other 19-thio-androstane derivatives according to the invention. Hydrolysis of the 19-acetylthio group gives the 19-thiol, which can be reacted with a hydrocarbyl, aralkyl, aryl or acyl halide to give 19-thio-androstane derivatives having the desired 19-substituent. Instead of an acyl halide also other functional derivatives of carboxylic acids can be used as an acyl anhydride.

The 19-thiol can also be obtained directly from the 19-sulphonate or 19-halo-derivative by reaction with MSH, wherein M is an alkalimetal, preferably sodium.

Another method of preparation starts from a 19-aldehyde. First, the 19-aldehyde group of such an androstane derivative is converted to a dialkylthio-acetal, after which one alkylthio group of the thioacetal obtained is reductively split off with the aid of a metal hydride, preferably in the presence of a Lewis acid (see, for example, Netherlands Pat. No. 6,405,765). This method is in particularly suitable for the preparation of the 19-thio-ethers according to the invention.

It is also possible to start from a 19-acid and to convert this 19-nor-androstane-19-carboxylic acid to the corresponding 19-thiol ester by treatment with N,N-dimethylphosphoramidine acid dichloride and triethylamine, followed by an alkanethiol. The thiol ester obtained is thereafter reduced with an LiAlH$_4$/AlCl$_3$ mixture in an ether (see, for example, Synth. Comm. 9(2), 91–96 (1979) and J. Org. Chem. 32, 1630–1631 (1967)).

A 19-hydroxy-androstane derivative can also be used as a starting material for the preparation of the novel 19-thioandrostane compounds. The 19-hydroxy group can be etherified with an alkanethiol, arylalkanethiol or arylthiol, under the action of trifluoroacetic acid. (In this case, in view of the acid character of the thiol compounds, this reaction can also be regarded as an "esterification"). It is also possible to treat a 19-hydroxy-androstane derivative with DCCI (dicyclohexylcarbodiimide) and an alkanethiol, thereby obtaining 19-alkylthio-androstanes (compare, for example, Ber. 107 (1974) p. 496).

For the introduction of the 19-hydrocarbyl-, 19-aralkyl- or 19-arylthio group, the starting material is usually a 3$\beta$-hydroxy-$\Delta^5$-androstene derivative, which after the introduction of the 19-thio group is converted into the 3-oxo-$\Delta^4$ system by oxidation, for example by Oppenauer-oxidation.

For the introduction of a 19-mercapto or 19-acylthio group, the starting material is usually a 3-oxo-$\Delta^4$-androstene derivative or the 4,5-dihydro analogue thereof.

After introduction of the 19-thio group, the substituents desired elsewhere in the steroid skeleton can still be introduced.

A $\Delta^1$ and/or $\Delta^6$ can, if desired, be introduced with the aid of chloranil or DDQ (dichlorodicyanobenzoquinone).

The substituents in position 17 can still be introduced or modified. For example, a 17-hydroxy group can be oxidised to the 17-oxo group by the Oppenauer method or with chromium trioxide. A 17-oxo group present can, if desired, be reduced to a 17-hydroxy group, for example with the aid of a complex metal hydride, such as sodium borohydride, in alkaline methanol, or be converted to the desired acetal group by reaction with, for example, ethylene glycol or 1,3-propanediol in the presence of triethyl orthoformate and paratoluenesulphonic acid.

The introduction of a hydrocarbyl group at position 17 is carried out by reacting the 17-oxo steroid with a metal derivative of a saturated or an unsaturated aliphatic hydrocabon, if necessary followed by a further conversion of the side chain thus introduced, e.g. reduction of an unsaturated group to a less unsaturated or a saturated group.

The metal derivative may be a Grignard compound, for example the magnesium bromide of the hydrocarbon concerned or an alkyl lithium compound. A particular form of the condensation reaction for producing the 17$\beta$-hydroxy-17$\alpha$-alkynyl compounds consists in that the 17-oxo steroid is reacted with a triple unsaturated hydrocarbon in the presence of an alkalimetal or an alkalimetal compound, for example an alkalimetal amide or -alcoholate or with an alkalimetal or earthalkalimetal compound of a triple unsaturated hydrocarbon.

The ester group in position 17 may be introduced by a method known per se, for example by reacting the 17$\beta$-hydroxy steroid with the acid concerned or a functional derivative thereof such as the anhydride or the halide or by reacting the reaction product obtained by the condensation of the 17-oxo steroid with a metal derivative of an unsaturated hydrocarbon radical without preliminary hydrolysis with the acid concerned or a functional derivative thereof. Esterification may, as an alternative, be performed by reacting the steroid with a carboxylic acid anhydride such as acetic acid anhydride in the presence of 4-dimethyl-aminopyridine, preferably also in the presence of a tertiary amine such as trimethylamine.

Etherification of the 17$\beta$-hydroxyl group may be performed according to standard procedures. Alkylethers may be prepared by reacting the 17-hydroxy compound with an alkylhalide, e.g. methyl iodide or ethyl iodide, in the presence of silver oxide or silver carbonate or in the presence of NaH in dimethylsulfoxide or tetrahydrofuran. The tetrahydropyranyl ether can be obtained by reacting the 17$\beta$-hydroxy steroid with dihydropyran in the presence of p-toluene sulphonic acid in a suitable solvent, such as tetrahydrofuran.

The 4,5-dihydro compounds may be obtained by reduction of the corresponding $\Delta^4$ compound, e.g. by hydrogenation on Pd/C, giving a mixture of 5$\alpha$-H and 5$\beta$-H compounds, which may be separated, e.g. by chromatography. Preferably, the 4,5-dihydro-5$\alpha$-H compound is obtained by hydrogenation of a 3$\beta$-OH-$\Delta^5$ derivative, giving the 3$\beta$-OH-5$\alpha$-H compound, whereafter the 3$\beta$-OH group is oxidised to the 3-oxo group, e.g. with chromic acid (Jones oxidation).

The invention is illustrated by the examples which follow.

EXAMPLE I (a) 7 g of potassium thioacetate were added to a solution of 7 g of 3β,19-dihydroxy-Δ⁵-androsten-17-one 3-acetate 19-tosylate (Chem. & Ind. 1963, p. 39) in 140 ml of dimethylformamide, after which the stirred solution was heated to 100° C. under a nitrogen atmosphere for 1 hour and 15 minutes. After having cooled to room temperature and been poured out into ice water, the reaction mixture was extracted with a mixture of methylene dichloride and tetrahydrofuran. After evaporating the extract, the residue was purified by chromatography over silica gel.

Yield: 2.4 g of 3β-hydroxy-19-acetylthio-Δ⁵-androsten-17-one.

(b) 513 mg of sodium methoxide were added to a stirred solution of 1.77 g of 3β-hydroxy-19-acetylthio-Δ⁵-androsten-17-one in 90 ml of methanol under a nitrogen atmosphere. After having been stirred for 3 hours at room temperature, the reaction mixture was neutralised with 50% strength acetic acid and poured out into ice water. Extraction with methylene dichloride/tetrahydrofuran, evaporation of the extract, chromatography of the residue over silica gel and recrystallisation from methylene dichloride/diethyl ether gave 0.53 g of 3β-hydroxy-19-mercapto-Δ⁵-androsten-17-one, of melting point 178.5°–180.5° C.

(c) 1.5 ml of cyclohexanone and a solution of 0.3 g of aluminium isopropoxide in 1 ml of dry toluene were added to a solution of 0.25 g of 3β-hydroxy-19-mercapto-Δ⁵-androsten-17-one in 10 ml of dry toluene. The mixture was boiled for 45 minutes under a nitrogen atmosphere. After addition of 1.6 g of sodium potassium tartrate, the reaction mixture was poured out into water and extracted with methylene dichloride. After evaporation of the extract, the residue was purified by chromatography over silica gel. Yield 0.24 g of 19-mercapto-Δ⁴-androstene-3,17-dione, melting point 141°–143° C., $[\alpha]_D^{20} = +142°$ (dioxane).

EXAMPLE II 56.6 mg of sodium methoxide and a solution of 0.035 ml of methyl iodide in 1.8 ml of methanol were added, under a nitrogen atmosphere, to a solution of 0.15 g of 19-mercapto-Δ⁴-androstene-3,17-dione in 5 ml of methanol. The mixture was then stirred for 15 minutes at room temperature and thereafter poured out into water and neutralised with acetic acid. The reaction mixture was extracted with methylene dichloride and after evaporation of the extract the residue was purified by crystallisation from methylene dichloride/diethyl ether. Yield: 0.1 g of 19-methylthio-Δ⁴-androstene-3,17-dione, melting point 160°–162.5° C., $[\alpha]_D^{20} = +185.6°$ (dioxane).

The corresponding 19-ethylthio compound (m.p. 120° C.; $[\alpha]_D^{20} = +184°$ in dioxane) and 19-propylthio compound were prepared in the same manner, by replacing methyl iodide by ethyl iodide and propyl iodide, respectively.

EXAMPLE III (a) 8.3 g of tosyl chloride were added, at 0° C., to a solution of 10 g of 19-hydroxy-testosterone-17-benzoate (Bull. Acad. Pol. Sci. Ser. Sci. Chim. 16 (6), (1968), p. 289–293) in 100 ml of pyridine. The reaction mixture was left to stand for 16 hours at room temperature. After addition of some ice, the reaction mixture was stirred for a further hour and was then diluted with water. The crystals which separated out were filtered off, washed with water, dried and recrystallised from acetone. Yield: 11.2 g of 19-hydroxy-testosterone 17-benzoate 19-tosylate, melting point 153°–155° C.

(b) Methylmercaptan was passed into 25 ml of dimethoxyethane at −5° C. until 300 mg had been absorbed. 3 ml of a 2N sodium methoxide solution in methanol were added to the mixture. After distilling off methanol in vacuo, 2.8 g of 19-hydroxytestosterone 17-benzoate 19-tosylate were added to the residue, with stirring, after which the reaction mixture was heated for 2 hours at 60° C. After it had cooled, the reaction mixture was poured out into 250 ml of water. The mixture obtained was acidified with 1N hydrochloric acid and extracted with methylene dichloride. The extract was washed until neutral, dried over sodium sulphate and evaporated in vacuo. The residue was chromatographed over silica gel. Yield: 0.9 g of 17β-hydroxy-19-methylthio-Δ⁴-androsten-3-one 17-benzoate.

(c) 0.3 g of 17β-hydroxy-19-methylthio-Δ⁴-androsten-3-one-17-benzoate were suspended in 20 ml of methanol. 0.3 g of KOH in 2 ml of water were added, after which the reaction mixture was boiled for 1 hour under a nitrogen atmosphere. Cooling, acidification with 2N hydrochloric acid and dilution with water, followed by extraction, evaporation of the extract and chromatographic purification gave 0.21 g of 17β-hydroxy-19-methylthio-Δ⁴-androsten-3-one, melting point 158° C., $[\alpha]_D^{20} = +113.6°$ (dioxane).

EXAMPLE IV 0.1 g of chromium trioxide was added to 5 ml of dry pyridine at 0° C. under a nitrogen atmosphere. After the mixture had been stirred for 10 minutes, 0.2 g of 17β-hydroxy-19-methylthio-Δ⁴-androsten-3-one dissolved in 2 ml of dry pyridine were added. After the reaction mixture had been stirred for 1 hour, it was poured out into 70 ml of water. The mixture was extracted 3 times with 10 ml of methylene dichloride and the combined extract was washed with 1N sulphuric acid until it gave a marked acid reaction and was then washed with water until neutral. After the extract had been dried and evaporated, the residue obtained was crystallised from a mixture of methylene dichloride and ether. Yield: 0.17 g of 19-methylthio-Δ⁴-androsten-3,17-dione, melting point 160°–162° C.; $[\alpha]_D^{20} = +185°$ (dioxane).

EXAMPLE V (a) 0.34 g of sodium methoxide, followed by a solution of 0.21 ml of methyl iodide in 10 ml of methanol, were added, under a nitrogen atmosphere, to a solution of 0.90 g of 3β-hydroxy-19-mercapto-Δ⁵-androsten-17-one in 30 ml of methanol.

The mixture was then stirred for 15 minutes at room temperature and subsequently poured out into 360 ml of water and neutralised with acetic acid. The reaction mixture was extracted with methylene dichloride (3×100 ml) and the extract was washed with 100 ml of water, dried over sodium sulphate and then evaporated. The residue was recrystallised from acetone/ether. Yield: 0.85 g of 3β-hydroxy-19-methylthio-Δ⁵-androsten-17-one.

(b) 0.5 ml of acetic anhydride was added to a solution of 0.85 g of 3β-hydroxy-19-methylthio-Δ⁵-androsten-17-one in 2 ml of dry pyridine. After it had been left to stand for 16 hours at room temperature, the reaction mixture was poured out into 20 ml of water. Extraction with methylene dichloride (3×10 ml) was followed by washing the combined extract with 1N sulphuric acid until an acid reaction was obtained. The extract was then washed with water until neutral and the neutral extract was dried over sodium sulphate and evaporated in vacuo. Crystallisation of the residue from acetone gave 0.78 g of 3β-hydroxy-19-methylthio-Δ⁵-androsten-17-one 3-acetate.

(c) 4.0 g of 3β-hydroxy-19-methylthio-Δ⁵-androsten-17-one 3-acetate were dissolved in 50 ml of methylene dichloride and 50 ml of ethylene glycol. 15 ml of triethyl orthoformate, followed by 50 mg of para-toluenesulphonic acid, were added to the solution. After having been boiled for 2 hours under reflux, the reaction mixture was cooled and poured out into 1 liter of 1% strength sodium bicarbonate solution in water. The methylene dichloride was separated off and the aqueous residue was additionally extracted 3 times with 100 ml of methylene dichloride. The combined extract was washed with water, dried over sodium sulphate and then evaporated to dryness. The dry residue of 4.5 gram, containing 3β-hydroxy-19-methylthio-Δ⁵-androsten-17-one 3-acetate 17-ethylene-acetal, was then reacted as described in Example V(d).

(d) 600 mg of potassium hydroxide in water were added to a solution of 4.5 g of crude 3β-hydroxy-19-methylthio-Δ⁵-androsten-17-one 3-acetate 17-ethylene-acetal in 90 ml of methanol. After the mixture had been left to stand for 4 hours at room temperature, 600 mg of acetic acid were added, after which half of the methanol was evaporated off in vacuo and the residue was diluted with 450 ml of water. Extraction with methylene dichloride (3×100 ml), washing the extract with water, drying over sodium sulphate and evaporation gave 4.1 g of 3β-hydroxy-19-methylthio-Δ⁵-androsten-17-one 17-ethylene-acetal.

(e) 4.1 g of 3β-hydroxy-19-methylthio-Δ⁵-androsten-17-one 17-ethylene-acetal were suspended in 200 ml of toluene. Thereafter, a solution of 15 g of aluminium isopropoxide in 54 ml of toluene was added, followed by 31 ml of cyclohexanone. This mixture was boiled under reflux for half an hour. The reaction was then stopped by adding 32 g of Seignette salt, after which the mixture was cooled and poured out into 1 liter of water. The mixture was extracted with a methylene dichloride/tetrahydrofuran mixture. After evaporation, the thin oil obtained was chromatographed over 250 g of silica gel, using a 7:3 toluene/ethyl acetate mixture as the eluant. The desired fractions were combined and evaporated to dryness in vacuo, and the residue was crystallised from acetone. Yield: 3.1 g of 19-methylthio-Δ⁴-androsten-3,17-dione 17-ethylene-acetal, oil with $[\alpha]_D^{20} = +59.2°$ (dioxane).

EXAMPLE VI (a) A solution of 120 mg NaOH in 1.2 ml methanol was added to a stirred solution of 1.4 g of 3β,19-dihydroxy-Δ⁵-androsten-17-one 3-acetate 19-tosylate in a mixture of 28 ml methanol and 45 ml tetrahydrofuran, at a temperature between 0° C. and 5° C. The reaction mixture was stirred for 3 hours at room temperature, then neutralised with acetic acid and poured out into ice-water. The precipitate was collected by suction and dried. Yield: 1.17 g 3β,19-dihydroxy-Δ⁵-androsten-17-one 19-tosylate, melting point 138°-139° C.; $[\alpha]_D^{20} = -36°$ (dioxane).

(b) In a nitrogen atmosphere 2.16 g CH₃SLi (obtained by reduction of dimethyl disulfide with lithium in liquid NH₃) were added to a solution of 4.58 g 3β,19-dihydroxy-Δ⁵-androsten-17-one 19-tosylate in 46 ml dimethylformamide. The mixture was stirred for 20 minutes at 70° C. and then poured out into ice-water. After stirring for 1 hour the precipitate was collected by suction. Yield: 3.0 g of 3β-hydroxy-19-methylthio-Δ⁵-androsten-17-one.

(c) In a way similar to that described in Example I(c) 3.0 g of 3β-hydroxy-19-methylthio-Δ⁵-androsten-17-one was oxidised and the product isolated by chromatography. Yield: 1.35 g 19-methylthio-Δ⁴-androsten-3,17-dione, melting point 160°-162.5° C., $[\alpha]_D^{20} = +185.6°$ (dioxane).

EXAMPLE VII

In a nitrogen atmosphere 0.29 g NaBH₄ was added to a stirred solution of 5 g 19-methylthio-Δ⁴-androsten-3,17-dione in a mixture of 60 ml tetrahydrofuran and 60 ml methanol, at a temperature of −12° C. This mixture was stirred for 30 minutes at −12° C. and then neutralised with acetic acid (50%) and poured out into ice-water. The mixture was extracted with methylene dichloride/tetrahydrofuran. After evaporation the residue was crystallised from methylene dichloride/diethyl ether. Yield: 3.4 g of 17β-hydroxy-19-methylthio-Δ⁴-androsten-3-one, melting point 156°-158° C., $[\alpha]_D^{20} = +113.6°$ (dioxane).

EXAMPLE VIII (a) In a nitrogen atmosphere and at 0° C. 0.9 ml hexanoyl chloride were added to a stirred solution of 1.0 g of 17β-hydroxy-19-methylthio-Δ⁴-androsten-3-one in 10 ml dry pyridine. The mixture was stirred overnight at room temperature and then poured out into ice-water and stirred for another 2 hours. Extraction with methylene chloride, evaporation of the extracts and chromatography of the residue gave 0.8 g 17β-hydroxy-19-methylthio-Δ⁴-androsten-3-one 17β-caproate, oil with $[\alpha]_D^{20} = +87.4°$ (dioxane).

(b) In a similar way by using decanoyl chloride and cyclo-octylacetyl chloride, respectively, instead of hexanoyl chloride the following 17β-esters were obtained:
17β-decanoate, oil with $[\alpha]_D^{20} = +76.9°$ (dioxane)
17β-cyclo-octylacetate, oil with $[\alpha]_D^{20} = +80.0°$ (dioxane).

EXAMPLE IX (a) In a nitrogen atmosphere 4.0 ml of propionic acid anhydride were added to a solution of 1.3 g of 19-mercapto-Δ⁴-androstene-3,17-dione in 65 ml of pyridine. The mixture was stirred overnight at room temperature, then stirred with ice for 1 hour and poured out into ice-water under simultaneous addition of 40 ml of 2N hydrochloric acid. Extraction with methylene dichloride, evaporation of the extracts and chromatography of the residue yielded 1.24 g of 19-propionylthio-Δ⁴-androstene-3,17-dione, oil with $[\alpha]_D^{20} = +176.8°$ (dioxane).

(b) In a similar way the following 19-acylthio compounds were prepared:
19-butyrylthio-Δ⁴-androstene-3,17-dione, oil with $[\alpha]_D^{20} = +168.7°$ (dioxane);
19-hexanoylthio-Δ⁴-androstene-3,17-dione, oil with $[\alpha]_D^{20} = +162.0°$ (dioxane);
19-pivaloylthio-Δ⁴-androstene-3,17-dione, melting point 115°-117° C., $[\alpha]_D^{20} = +173.8°$ (dioxane);

19-cyclo-octylacetylthio-$\Delta^4$-androstene-3,17-dione, oil with $[\alpha]_D^{20} = +148.9°$ (dioxane);
19-dodecanoylthio-$\Delta^4$-androstene-3,17-dione.

EXAMPLE X (a) To a suspension of 3.18 g of 19-mercapto-$\Delta^4$-androstene-3,17-dione in 100 ml of methanol were added 1.19 g of NaOCH$_3$ and 1.04 ml of allyl bromide. After stirring for 20 minutes at room temperature the reaction mixture was poured out into 3.2 liters of ice-water, acidified with 32 ml of acetic acid. After 1 hour the precipitate was collected by suction and crystallised from methylene chloride/diethyl ether. Yield: 3.04 g of 19-allylthio-$\Delta^4$-androstene-3,17-dione, melting point 140°–142.5° C., $[\alpha]_D^{20} = +190.9°$ (dioxane).

(b) In a similar way, using butyl bromide and benzyl bromide, respectively, instead of allyl bromide, the following compounds were obtained:
19-butylthio-$\Delta^4$-androstene-3,17-dione, oil with $[\alpha]_D^{20} = +173.8°$ (dioxane);
19-benzylthio-$\Delta^4$-androstene-3,17-dione, melting point 123°–124° C., $[\alpha]_D^{20} = +155.1°$ (dioxane).

EXAMPLE XI

In a nitrogen atmosphere 3.25 g of C$_2$H$_5$SNa were added to a solution of 4.43 g of 3$\beta$,19-dihydroxy-$\Delta^5$-androsten-17-one 19-tosylate in 88 ml of dimethylformamide. The mixture was stirred for 1 hour at 70° C. After cooling the mixture was poured out into ice-water. Extraction with methylene dichloride/tetrahydrofuran, evaporation of the extracts and chromatography over silica gel yielded 3.16 g of 3$\beta$-hydroxy-19-ethylthio-$\Delta^5$-androsten-17-one. Oppenauer oxidation of this product as described in Example I(c) and crystallisation of the oxidised product gave 1.3 g of 19-ethylthio-$\Delta^4$-androstene-3,17-dione, melting point 117°–120° C., $[\alpha]_D^{20} = +184.2°$ (dioxane).

EXAMPLE XII

In a nitrogen atmosphere 1.04 g of sodium thiophenolate were added to a solution of 1.84 g of 3$\beta$,19-dihydroxy-$\Delta^5$-androsten-17-one 19-tosylate in 37 ml of dimethylformamide. The mixture was stirred for 1 hour at 80° C., then cooled and poured out in ice-water, acidified with 0.6 ml of acetic acid. Extraction with methylene chloride/tetrahydrofuran, evaporation of the extracts and chromatography of the residue yielded 0.9 g of 3$\beta$-hydroxy-19-phenylthio-$\Delta^5$-androsten-17-one which on Oppenauer oxidation and chromatography in a way similar to that described in Example I(c) gave 0.5 g of 19-phenylthio-$\Delta^4$-androstene-3,17-dione, oil with $[\alpha]_D^{20} = ;190.3°$ (dioxane).

EXAMPLE XIII

In a nitrogen atmosphere 2.1 g of chloranil were added to a stirred solution of 3 g of 19-methylthio-$\Delta^4$-androsten-3,17-dione in a mixture of 24 ml of glacial acetic acid and 6 ml of toluene. The reaction mixture, while stirring, was heated on an oilbath of 120° C. for 2 hours. After cooling and dilution with water, the mixture was extracted with methylene dichloride. Evaporation of the extracts and chromatography of the oily residue over silica gel gave 1.8 g of 19-methylthio-$\Delta^{4,6}$-androstadien-3,17-dione, amorphous, $[\alpha]_D^{20} = +157.8°$ (dioxane).

EXAMPLE XIV (a) In a nitrogen atmosphere a mixture of 4 g of 19-hydroxy-$\Delta^4$-androstene-3,17-dione 19-tosylate (Steroids 4, 1964, p. 1) and 5 g of potassium thioacetate in 70 ml of dimethylformamide were stirred for 16 hours at 100° C. After cooling and pouring out in water the mixture was extracted with methylene dichloride/tetrahydrofuran. Evaporation of the extracts and chromatography of the residue gave 1.55 g of 19-acetylthio-$\Delta^4$-androstene-3,17-dione, oil with $[\alpha]_D^{20} = +170.2°$ (dioxane).

(b) In a nitrogen atmosphere 0.5 g of NaOCH$_3$ were added to a stirred solution of 3.1 g of 19-acetylthio-$\Delta^4$-androstene-3,17-dione in 155 ml of methanol. After stirring for 30 minutes the reaction mixture was neutralised with acetic acid (50%) and poured out into ice-water. The precipitate was sucked off and crystallised from methylene dichloride/diethyl ether. Yield: 1.72 g of 19-mercapto-$\Delta^4$-androstene-3,17-dione, melting point 141°–143° C., $[\alpha]_D^{20} = +142°$ (dioxane).

(c) In a way similar to that described in Example VII 1 g of 19-mercapto-$\Delta^4$-androstene-3,17-dione was reduced to give 0.57 g of 17$\beta$-hydroxy-19-mercapto-$\Delta^4$-androsten-3-dione, melting point 113°–115° C., $[\alpha]_D^{20} = +65.2°$ (dioxane).

EXAMPLE XV

Acetylene was introduced into a suspension of 5.9 g potassium t.-butoxide in 26 ml of tetrahydrofuran, at a temperature between 0° C. and 5° C. and for 30 minutes. To this mixture a solution of 1.5 g of 3$\beta$-hydroxy-19-methylthio-$\Delta^5$-androsten-17-one in 15 ml tetrahydrofuran was added, whereafter for 45 minutes acetylene was led through the reaction mixture. Excess acetylene was swept out of the mixture with nitrogen, whereafter the mixture was neutralised with 2N sulphuric acid. Extraction with methylene dichloride, evaporation of the extracts and chromatography of the residue gave 0.5 g of 17$\alpha$-ethinyl-19-methylthio-$\Delta^5$-androstene-3$\beta$,17$\beta$-diol, which on Oppenauer oxidation according to the method described in Example I(c) gave 17$\alpha$-ethinyl-17$\beta$-hydroxy-19-methylthio-$\Delta^4$-androsten-3-one.

EXAMPLE XVI

Hydrogen was led through a solution of 0.5 g of 3$\beta$-hydroxy-19-methylthio-$\Delta^5$-androsten-17-one in 100 ml of methanol in the presence of 0.1 g of prehydrogenated Pd/C (10%). After the reaction the catalyst was filtered off and the filtrate evaporated until small volume. Chromatography of the residue yielded 3$\beta$-hydroxy-19-methylthio-5$\alpha$-androstan-17-one, which on oxidation in 50 ml of acetone with 0.5 ml of 8N chromic acid solution, addition of methanol, pouring out in water, extraction and chromatography gave 19-methylthio-5$\alpha$-androstane-3,17-dione.

Administration of the compounds of the present invention to patients can be in the form of oral, intramuscular, intravenous or subcutaneous pharmaceutical compositions.

Materials for use as pharmaceutical carriers for oral administration are composed of carriers or diluents, such as lactose: binders such as amylopectin or polyvinyl-pyrrolidone: antioxidants such as ascorbylpalmitate, or dl-$\alpha$-tocopherol: disintegrants such as wheat starch or potato starch: and/or lubricants such as magnesium stearate, stearic acid or colloidal silica. For injection (i.m., i.v., s.c.) oil type solutions are used, based on e.q. peanut oil, olive oil or sesame oil, containing antioxidants such as butylated hydroxytoluene and/or butylated hydroxy anisole, or use is made of suspension type injectables based on water containing antioxidants such as sodium bisulphite, and, e.g., suspending agents such as sodium carboxymethyl cellulose.

Individual dosage units for oral administration contain from 1.0 to 500 mg of the aromatase inhibitor. Daily dosages of from 5 to 1000 mg, preferably from 10 to 200 mg of the aromatase inhibitor are recommenced. For example, a tablet containing 10 mg of the active substance, administered three times a day is suitable. For injection, proposed suspensions or solutions are used which contain from 10 to 250 mg/ml of the aromatase inhibitor.

We claim:

1. Novel 19-thio-androstane derivatives having the general formula:

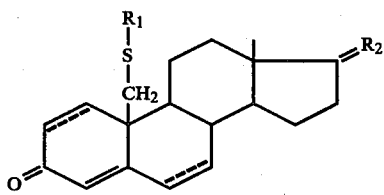

and the 4,5-dihydro analogues thereof, wherein $R_1$=H, hydrocarbyl(1–4C), aralkyl (7–9C), aryl(-6–9C) or acyl derived from an organic carboxylic acid having 1–18 atoms;

$R_2$=O, $\alpha R_4(\beta R_3)$ or an acetyl group;

$R_3$=a free, esterified or etherified hydroxyl group; and $R_4$=H or hydrocarbyl(1–4C);

and wherein the broken lines indicate the optional presence of a double bond in the 1,2-position and/or 6,7-position.

2. Compounds according to claim 1, wherein $R_1$=methyl or ethyl.

3. Compounds according to claim 1 wherein $R_2$=O.

4. Compounds according to claim 1 wherein $R_2=\alpha R_4(\beta R_3)$, $R_4$=H and $R_3$ is OH.

5. Compounds according to claim 1 wherein $R_2=\alpha R_4(\beta R_3)$, $R_3$=OH and $R_4$ is ethinyl or allyl.

6. 4,5-Dihydro compounds according to claim 1 wherein the 5-H atom is in α-position.

7. A method of controlling oestrogen production in mammals which comprises administering to said mammal an aromatase-inhibiting effective amount of one or more 19-thio-androstane compounds as defined in claim 1 in a suitable pharmaceutical carrier.

8. A pharmaceutical composition for controlling oestrogen formation in mammals having as its active ingredient one or more 19-thio-androstane compounds as defined in claim 1, in a suitable pharmaceutical carrier.

9. Compounds according to claim 2, wherein $R_2$=O.

10. Compounds according to claim 2, wherein $R_2=\alpha R_4(\beta R_3)$, $R_4$=H and $R_3$ is OH.

11. Compounds according to claim 2, wherein $R_2=\alpha R_4(\beta R_3)$, $R_3$=OH and $R_4$ is ethinyl or allyl.

12. 4,5-Dihydro compounds according to claim 2 wherein the 5-H atom is in α-position.

13. 4,5-Dihydro compounds according to claim 3 wherein the 5-H atom is in α-position.

14. 4,5-Dihydro compounds according to claim 4 wherein the 5-H atom is in α-position.

15. 4,5-Dihydro compounds according to claim 5 wherein the 5-H atom is in α-position.

16. 4,5-Dihydro compounds according to claim 9 wherein the 5-H atom is in α-position.

17. 4,5-Dihydro compounds according to claim 10 wherein the 5-H atom is in α-position.

18. 4,5-Dihydro compounds according to claim 11 wherein the 5-H atom is in α-position.

19. 4,5-Dihydro compounds according to claim 12 wherein the 5-H atom is in α-position.

* * * * *